United States Patent
Tang et al.

(10) Patent No.: US 6,344,039 B1
(45) Date of Patent: *Feb. 5, 2002

(54) DEVICE FOR ELIMINATING PARALLAX OF STEREO MICROSCOPES DURING REFRACTIVE LASER SURGERY

(75) Inventors: Fuqian Tang, Orlando; David Voorhees, Oviedo, both of FL (US)

(73) Assignee: LaserSight Technologies, Inc., Winter Park, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/819,730

(22) Filed: Mar. 18, 1997

(51) Int. Cl.⁷ .............................................. A61H 18/20
(52) U.S. Cl. ............................... 606/4; 606/10; 606/13; 359/368; 359/377; 359/831; 359/835
(58) Field of Search ........................... 606/2–6, 10, 13, 606/14, 18, 19; 359/368, 382, 384, 385, 389, 831, 835, 836, 377

(56) References Cited

U.S. PATENT DOCUMENTS

| | | | |
|---|---|---|---|
| 3,828,788 A | * | 8/1974 | Krasnov et al. ............... 606/18 |
| 4,520,816 A | | 6/1985 | Schachar et al. |
| 4,573,467 A | | 3/1986 | Rich et al. |
| 4,638,801 A | | 1/1987 | Daly et al. |
| 4,865,441 A | * | 9/1989 | Reis ............................... 606/4 |
| 5,163,936 A | | 11/1992 | Black et al. |
| 5,425,729 A | | 6/1995 | Ishida et al. |
| 5,442,487 A | | 8/1995 | Mizuno |

FOREIGN PATENT DOCUMENTS

| | | | | |
|---|---|---|---|---|
| DE | 3212691 | * | 10/1983 | ................. 359/377 |
| WO | 9101703 | * | 2/1991 | ................... 606/18 |

OTHER PUBLICATIONS

D. Eimerl, L. Davis, & S. Vlesko, Optical, mechanical, and thermal properties of barium borate, Journal of Applied Physics, Sep. 1987, pp. 1968–1983.

J.T. Lin, Non–linear crystals for tunable coherent sources, Optical and Quatum Electronics, 1990, pp. S283–S313.

J.T. Lin, Temperature–tuned noncritically phase–matched frequency conversion in LiB3O5 crystal, Optics Communications, Dec. 1990, pp. 159–165.

Y. Tanaka, H. Kuroda, & S. Shionoya, Generation of Tunable Picsecond Pulses in the Ultraviolet Region Down to 197nm, May 1982, pp. 434–436.

* cited by examiner

Primary Examiner—David M. Shay
(74) Attorney, Agent, or Firm—William H. Bollman

(57) ABSTRACT

A device for eliminating decentration error due to parallax during ophthalmic laser surgery comprises a stereo microscope having a first ocular and a second ocular and an objective lens for viewing a patient's eye, a laser for projecting a laser beam at a patient's eye during ophthalmic laser surgery; and structure for aligning the objective lens relative to the first ocular to center the laser beam with a patient's eye. The device for eliminating decentration error due to parallax also comprises prism positioned between either the first ocular and the objective lens or the objective lens and the laser beam.

10 Claims, 3 Drawing Sheets

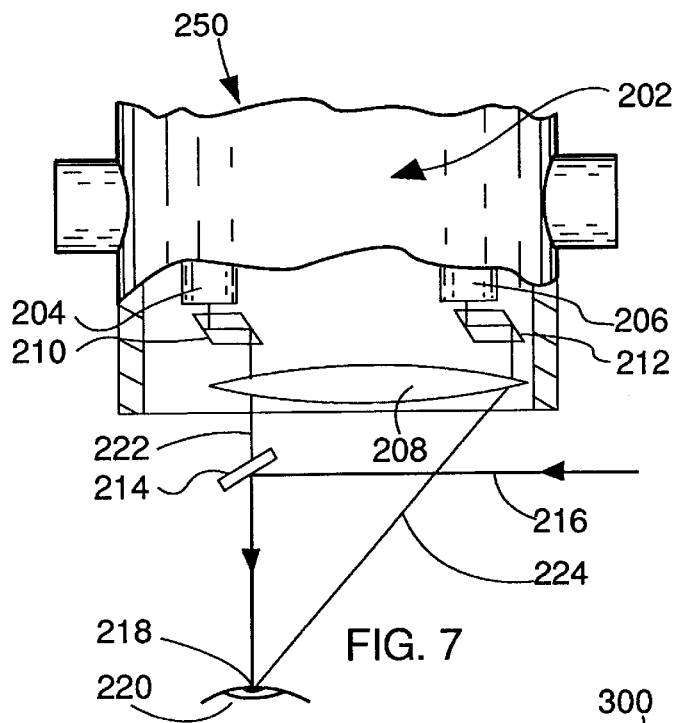
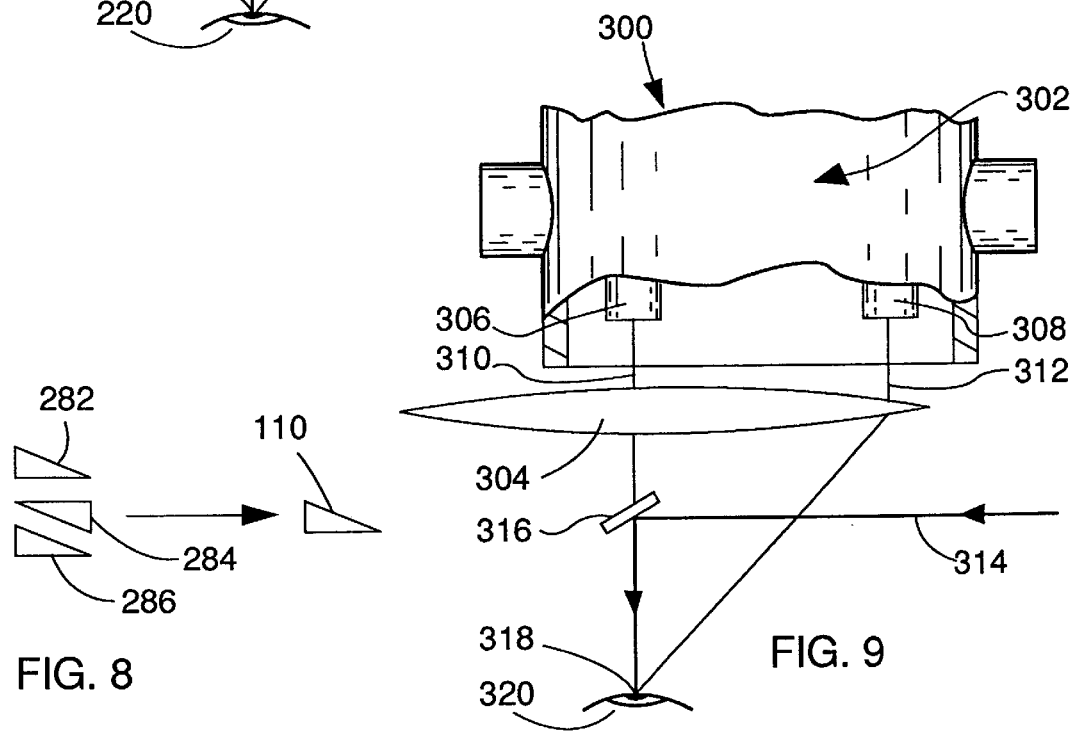

DEVICE FOR ELIMINATING PARALLAX OF STEREO MICROSCOPES DURING REFRACTIVE LASER SURGERY

BACKGROUND OF THE INVENTION

The present invention relates generally to ophthalmic refractive laser surgery systems and more particularly to a device for eliminating the parallax of a stereo microscope which is utilized in an ophthalmic refractive laser surgery system.

Lasers have been utilized in ophthalmic surgery to ablate the cornea of the eye in order to correct for abnormal conditions of the eye. Precise centering of the eye is critical in ophthalmic refractive laser surgery for effective treatment. In such laser surgical procedures a stereo microscope or a biomicroscope is used by a surgeon to precisely center the eye prior to aiming and focusing a laser beam on the cornea to be ablated. Incorrect positioning or centering of the eye prior to ablating the cornea can result in a less ideal operation. It is known that the use of a stereo microscope introduces a phenomenon known as parallax error. Parallax error can easily cause decentration of treatment, especially for inexperienced surgeons. Since centering of the eye is extremely important, it is desirable to utilize a device to eliminate any parallax caused by use of the stereo microscope.

The present invention is designed to obviate and overcome many of the disadvantages and shortcomings experienced with use of a stereo microscope, and to provide a device for eliminating parallax of a stereo microscope during refractive laser surgery. The present invention is intended to eliminate any parallax error associated with the use of a stereo microscope and to provide a device which provides perfect centering of the eye prior to use of a laser to ablate the eye.

SUMMARY OF THE INVENTION

The present invention is a device for eliminating decentration error due to parallax during ophthalmic laser surgery which comprises a stereo microscope having a first ocular and a second ocular and an objective lens for viewing a patient's eye, a laser for projecting a laser beam at a patient's eye during ophthalmic laser surgery, and means for aligning the objective lens relative to the first ocular to center the laser beam with a patient's eye.

In another embodiment of the present invention, a device for eliminating decentration error due to parallax during ophthalmic laser surgery is disclosed which comprises a stereo microscope having a first ocular and a second ocular and an objective lens for viewing a patient's eye, a laser for projecting a laser beam at a patient's eye during ophthalmic laser surgery, and means positioned between the objective lens and the first ocular to center the laser beam on a patient's eye.

In yet another embodiment of the present invention, a device for eliminating decentration error due to parallax during ophthalmic laser surgery is disclosed which comprises a stereo microscope having a pair of oculars and an objective lens for viewing a patient's eye, a laser for projecting a laser beam at a patient's eye during ophthalmic laser surgery, and means positioned between the objective lens and the laser beam to center the laser beam on a patient's eye.

In light of the foregoing comments, it will be recognized that a principal object of the present invention is to provide a device for eliminating parallax of a stereo microscope.

Another object of the present invention is to provide a device for eliminating parallax of a stereo microscope which is of simple construction and design and which can be easily employed with highly desirable results.

A further object of the present invention is to provide a device for eliminating parallax of a stereo microscope ensures precise aiming and focusing of a laser beam to ablate a cornea of an eye.

These and other objects and advantages of the present invention will become apparent after considering the following detailed specification in conjunction with the accompanying drawings, wherein:

BRIEF DESCRIPTION OF THE DRAWINGS

FIG. 7 is a partial perspective view of a fourth preferred embodiment constructed according to the present invention;

FIG. 8 is a perspective view of a plurality of wedge-shaped prisms combined to produce an equivalent of a single wedge-shaped prism; and FIG. 9 is a partial perspective view of a sliding mechanism that is used to reposition the microscope and prisms from a center position to a position where a laser mirror and a laser beam are vertically aligned with a reference line of sight.

DESCRIPTION OF THE PREFERRED EMBODIMENTS

Figure 1:
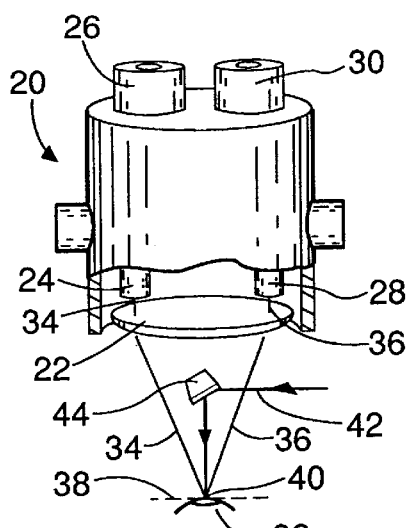
FIG. 1 is a perspective view, shown partially in cross-section, of some of the components of a typical ophthalmic laser surgery system with a patient's eye positioned at a focal plane.

Referring now to the figures, wherein like numerals refer to like items, reference is now made to FIG. 1 where a typical stereo microscope 20 is shown which is used in conjunction with a laser system (not shown) to perform ophthalmic refractive laser surgery. The stereo microscope 20 includes an objective lens 22, a left ocular 24 and an associated left eye piece 26, and a right ocular 28 and its associated right eye piece 30. A surgeon typically looks through the eye pieces 26 and 30, the oculars 24 and 28, and the objective lens 22 at a patient's eye 32. Frequently there is a reticule (not shown) in either of the eye pieces 26 or 30 which is used by the surgeon to center the eye 32. The surgeon effectively has a left line of sight, which is represented by a line 34, and a right line of sight, which is represented by a line 36. Assuming that the left eye piece 26 has the reticule, the surgeon would use the left line of sight 34 as the centration reference. When the patient's eye 32 is tangent to a focal plane, represented by a dashed line 38, the left line of sight 34 is centered on a center 40 of the eye 32 when the surgeon uses an apex of the cornea for centration.

Additionally, a laser beam 42, which is reflected by a mirror 44 onto the eye 32, will also be coincidental with the center 40 of the eye 32 and the left line of sight 34. In this particular case with the eye 32 tangent to the focal plane 38, the laser beam 42 will treat the center 40 of the eye 32 and there is no error due to parallax.

Figure 2:
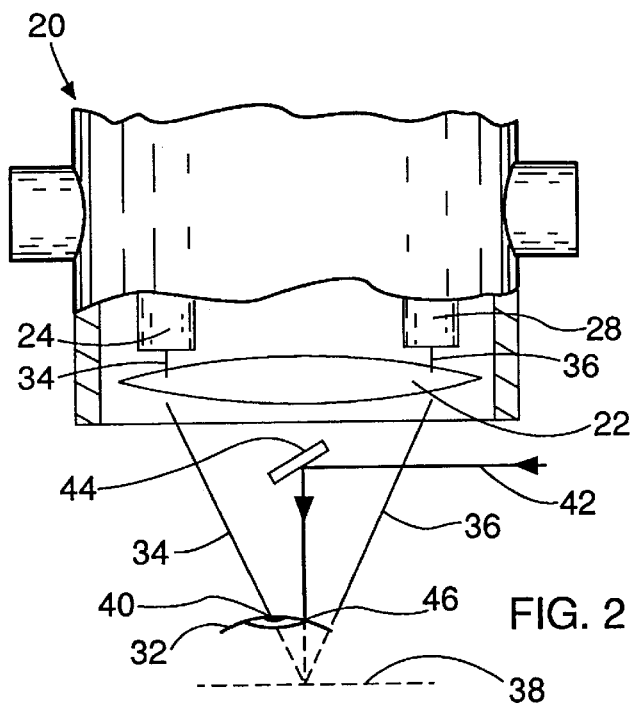
FIG. 2 is a partial perspective view showing decentration error caused by parallax in an ophthalmic laser surgery system that occurs when the center of a patient's eye is above a focal plane.

The following situation illustrates one cause of decentration which occurs with the use of a stereo microscope 20. In FIG. 2, the patient's eye 32 is positioned above the focal plane 38 which forces the surgeon to move the eye 32 into a position where the eye 32 is off centered. For example, assuming again that the reticule is in the left eye piece 26 and the apex of the cornea is used for centration, the surgeon will move the eye 32 until the center 40 of the eye 32 is coincident with the left line of sight 34. In this case, the laser beam 42, as reflected by the mirror 44, is off center at a point 46 and does not treat the center 40 of the eye 32. Similarly, decentration will occur when the eye 32 is below the focal plane 38.

Figure 3:
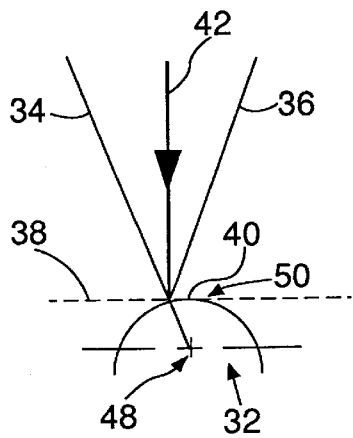
FIG. 3 is a partial side view of a patient's eye showing decentration error caused by parallax when the apex of the patient's cornea is at a focal plane.

FIG. 3 illustrates the center 40 of the eye 32 which includes an iris center 48 and a cornea plane 50. Another example of how decentration error can occur is due to the difference between the cornea plane 50 and the iris center 48. Sometimes, a surgeon will view the center 40 of the eye 32 as being the iris center 48 because the surface of the cornea is almost invisible due to its transparency and clarity. However, the iris center 48 is about 3 mm below the cornea plane 50. This will result in the area treated by the laser beam 42 being off centered. It is apparent that the decentration problems described with respect to FIGS. 2 and 3 are caused by the surgeon looking at the eye 40 from an angle or parallax while the laser beam 42 which treats the eye 32 is directed straight down to the eye 32.

Figure 4:
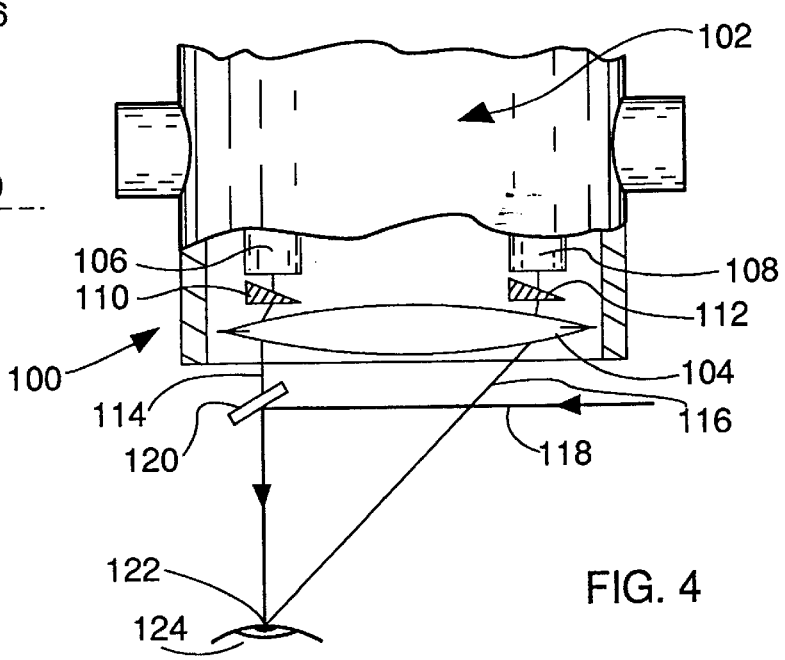
FIG. 4 is a partial perspective view of a preferred embodiment of the present invention.

Referring now to FIG. 4, a first preferred embodiment of a device 100 for eliminating parallax is shown which shows a stereo microscope 102 having an objective lens 104, a left or first ocular 106, and a right or second ocular 108. A left eye piece (not shown) is associated with the left ocular 106 and the left eye piece may include a reticule, which is also not shown. Alternatively, the right ocular 108 may have associated with it a right eye piece (not shown). The right eye piece may also have a reticule through which a surgeon may look. The stereo microscope 102 further comprises a left wedge shaped prism 110 positioned between the left ocular 106 and the objective lens 104 and a right wedge shaped prism 112 positioned between the right ocular 108 and the objective lens 104. A surgeon has a left line of sight, which is represented by a line 114 and a right line of sight, which is represented by a line 116. A laser beam 118 is reflected by a reflecting mirror 120 onto a center 122 of a patient's eye 124.

It is important to note that the left line of sight 114 at the cornea is perpendicular to the eye 124 and coincident with the laser beam 118. The left line of sight 114 follows a path through the left ocular 106, the prism 110, the objective lens 104, the reflecting mirror 120 onto the eye 124. In this arrangement the left line of sight 114 is coincident with the laser beam 118 and the laser beam 118 is centered on the eye 124. The prism 110 is used to eliminate any decentration error due to the parallax associate with the use of the stereo microscope 102. Additionally, if the surgeon determines that the right line of sight 116 should be employed for centering the eye 124, then the prisms 110 and 112 are reversed in orientation and the stereo microscope 102 will be moved such that the right line of sight 116 is perpendicular to the eye 124 and coincident with the laser beam 118. The right line of sight 116 will follow the path through the right ocular 108, the prism 112, the objective lens 104, the reflecting mirror 120 and finally onto the eye 124.

Figure 5:
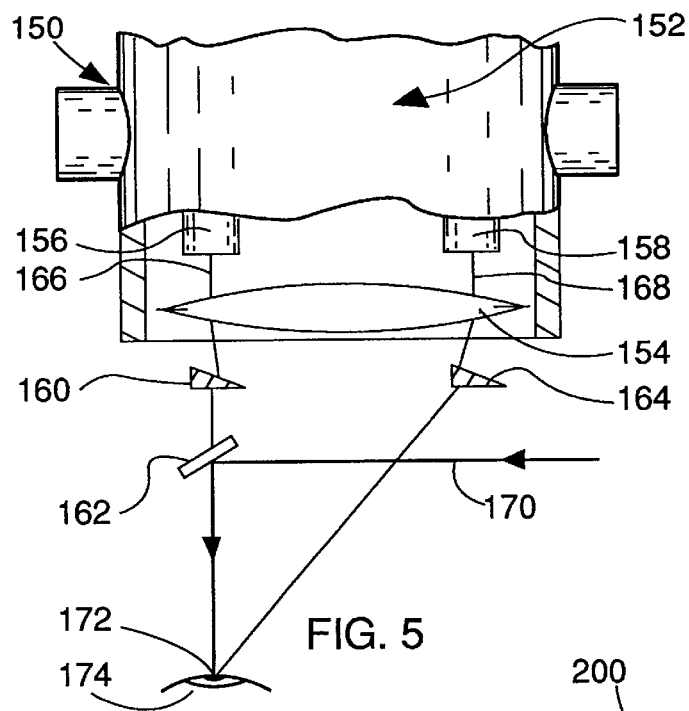
FIG. 5 is a partial perspective view of a second preferred embodiment of the present invention.

A second preferred embodiment of a device 150 for eliminating parallax is shown in FIG. 5 which illustrates a stereo microscope 152 having an objective lens 154, a left ocular 156, and a right ocular 158. A left eye piece (not shown) is associated with the left ocular 156 and the left eye piece may include a reticule, which is also not shown. Alternatively, the right ocular 158 may have associated with it a right eye piece (not shown). The right eye piece may also have a reticule through which a surgeon may look. The stereo microscope 152 further comprises a left wedge shaped prism 160 positioned between the objective lens 154 and a reflecting mirror 162. A right wedge shaped prism 112 is also positioned between the objective lens 154 and the reflecting mirror 162. A surgeon has a left line of sight, which is represented by a line 166 and a right line of sight, which is represented by a line 168. A laser beam 170 is reflected by the reflecting mirror 162 onto a center 172 of a patient's eye 174.

Again, it should be recognized that left line of sight 166 at the cornea is perpendicular to the eye 174 and coincident with the laser beam 170. The left line of sight 166 follows a path through the left ocular 156, the objective lens 154, the prism 160, and the reflecting mirror 162 onto the eye 174. In this arrangement the left line of sight 166 is coincident with the laser beam 170 and the laser beam 170 is centered on the eye 174. The prism 160 is used to eliminate any decentration error due to the parallax associate with the use of the stereo microscope 152. Additionally, if the surgeon prefers to use the right line of sight 168 for centering the eye 174, then the prisms 160 and 164 are reversed in orientation and the stereo microscope 152 is moved such that the right line of sight 168 at the cornea is perpendicular to the eye 174 and coincident with the laser beam 170. The right line of sight 168 will follow the path through the right ocular 158, the objective lens 154, the prism 164, and the reflecting mirror 162 and finally onto the eye 174.

Figure 6:
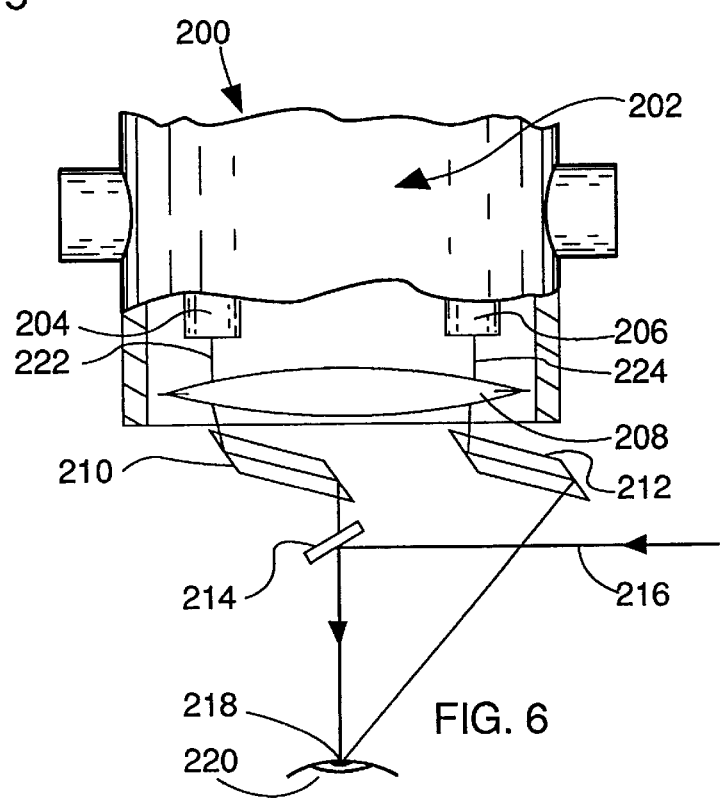
FIG. 6 is a partial perspective view of a third preferred embodiment of the present invention.

A further preferred embodiment of a device 200 for eliminating parallax is shown in FIG. 6. The device 200 comprises a stereo microscope 202 having a left ocular 204 and a right ocular 206. Positioned below the left and right oculars 204 and 206 is an objective lens 208 and located below the objective lens is a left prism 210 and a right prism 212. Both of the prisms 210 and 212 are in the shape of a parallelogram. A reflecting mirror 214 is used to reflect a laser beam 216 onto a center 218 of a patient's eye 220. A left line of sight 222 follows a path through the left ocular 204, the objective lens 208, the prism 210, the reflecting mirror 214, and onto the center 218 of the eye 220. A right line of sight 224 is also shown which is directed through the right ocular 206, the objective lens 208, the prism 212 and onto the eye 220. With the arrangement shown in FIG. 6 the left line of sight 222 at the cornea is perpendicular to the eye 220 and coincident with the laser beam 216 and it is possible to correctly align the laser beam 216 with the center 218 of the patient's eye 220 by having the surgeon look through the left ocular 204 and moving the patients' eye 220 into a position wherein the center 218 is aligned with the laser beam 216. In this particular embodiment, the stereo microscope 202 does not have to be repositioned with respect to the reflecting mirror 214.

Another preferred embodiment of a device 250 for eliminating parallax is depicted in FIG. 7. The device 250 is similar to the device 200 with the exception being that the prisms 210 and 212 have been positioned between the oculars 204 and 206 and the objective lens 208. Again, left line of sight 222 is perpendicular to the eye 220 and coincident with the laser beam 216. The stereo microscope 202 in the device 250 does not have to be moved in order to correctly and accurately align the center 218 of the eye 220 for treatment by the laser beam 216.

With reference now to FIG. 8, there is shown a prism 280 which is comprised of three wedge shaped prisms 282, 284, and 286 which are combined together and which may be a substitute or a replacement for the prism 110. The prisms 282, 284, and 286 are each made of different materials having different color dispersion characteristics and the resultant prism 280 has no color dispersion. Additionally, the prism 280 may be a suitable replacement for the prisms 112, 160, or 164. Although three wedge shaped prisms 282, 284, and 286 are shown to be combined to form the prism 280 it is also possible to form the prism 280 from two wedge shaped prisms or even four or more wedge shaped prisms.

FIG. 9 illustrates another embodiment of the present invention that does not require prisms. In this embodiment the device for eliminating parallax 300 comprises a stereo microscope 302 having an objective lens 304, a left ocular 306, and a right ocular 308. The left ocular 306 has a left eye piece, not shown, and the left eye piece may also include a reticule, also not shown. The right ocular 308 further has associated with it a right eye piece, not shown, and a reticule may be included in the right eye piece. The left ocular 306 has a left line of sight 310 and the right ocular 308 has a right line of sight 312. A laser beam 314 is reflected by a reflecting mirror 316 onto a center portion 318 of a patient's eye 320.

The objective lens 304 is a large lens and spans most of the stereo microscope 302. In order to eliminate parallax the stereo microscope 302 is moved relative to the objective lens 304 so that the left ocular 306 is centered directly over the center of the objective lens 304. In this position parallax is completely eliminated and a surgeon may confirm that the laser beam 316 is centered on the patient's eye 320. Additionally, the stereo microscope 302 may be moved relative to the objective lens 304 so that the right ocular 308 is centered directly over the center of the objective lens 304. In this position a surgeon would use the right line of sight 312 to verify that the laser beam 314 is centered on the patient's eye 320. When viewing through either the left ocular 306 or the right ocular 308 it may be required that a lens cap (not shown) be used to block a surgeon's line of sight through the ocular 306 or 308 which is not being used to center the laser beam 314. Additionally, it is also possible to have the stereo microscope 302 stationary and the objective lens 304 may be movable relative to the stereo microscope 302. Although most commonly available stereo microscopes are movable and it will be the objective lens 304 which will be movable or repositionable relative to the stereo microscope 302.

From all that has been said, it will be clear that there has thus been shown and described herein a device for eliminating parallax which fulfills the various objects and advantages sought therefor. It will be apparent to those skilled in the art, however, that many changes, modifications, variations, and other uses and applications of the subject device for eliminating parallax are possible and contemplated. All changes, modifications, variations, and other uses and applications which do not depart from the spirit and scope of the invention are deemed to be covered by the invention, which is limited only by the claims which follow.

What is claimed is:

1. A device for eliminating decentration error due to parallax during ophthalmic laser surgery comprising:

a stereo microscope having a first ocular, a second ocular, and an objective lens adapted to view a patient's eye;

a laser adapted to project an ablating laser beam onto a surface of a patient's eye;

a first prism oriented in a first direction in a first optical path including said first ocular; and a second prism oriented in said first direction in a second optical path including said second ocular;

wherein one of said first and second optical paths is subsequently normal to a surface of said patient's eye while the other of said first and second optical paths is at an acute angle relative to said surface of said patient's eye.

2. A device for eliminating decentration error due to parallax during ophthalmic laser surgery comprising:

a stereo microscope having a first ocular, a second ocular, and an objective lens adapted to view a patient's eye;

a laser adapted to project an ablating laser beam at said patient's eye;

a first prism oriented in a first direction in a first optical path including said first ocular; and a second prism oriented in said first direction in a second optical path including said second ocular;

wherein said ablating later beam travels a common optical path with a portion of a singular ocular.

3. A device for eliminating decentration error due to parallax during ophthalmic laser surgery comprising:

a stereo microscope having a first ocular, a second ocular, and an objective lens adapted to view a patient's eye;

a laser adapted to project an ablating laser beam at said patient's eye;

a first prism oriented in a first direction in a first optical path including said first ocular; and a second prism oriented in said first direction in a second optical path including said second ocular;

wherein said first and said second prisms are oriented such that each corresponding side of said first prism faces a same direction as each corresponding side of said second prism, in the respective optical paths.

4. The device of claim 3, wherein:

said first prism and said second prism are each formed by stacking at least two wedge shaped prisms.

5. The device of claim 3, wherein:

said first prism is positioned between said first ocular and said objective lens.

6. The device of claim 3, wherein:

said means for providing said line of sight is positioned between said objective lens and said patient's eye.

7. The device of claim 3, wherein:

said first prism and said second prism are each a parallelogram prism.

8. The device of claim 3, wherein:

said first prism is positioned between said objective lens and said patient's eye.

9. The device of claim 3, wherein:

said first prism and second prism are each wedge shaped prisms.

10. The device of claim 7, wherein:

said at least two wedge shaped prisms each have a different color dispersion characteristic.

* * * * *